United States Patent [19]

Dasgupta et al.

[11] Patent Number: 5,433,838
[45] Date of Patent: Jul. 18, 1995

[54] ELECTROPHORESIS WITH CHEMICALLY SUPPRESSED DETECTION

[75] Inventors: Purnendu Dasgupta; Bao Li-Yuan, both of Lubbock, Tex.

[73] Assignee: The Dow Chemical Company, Midland, Mich.

[21] Appl. No.: 258,126

[22] Filed: Jun. 10, 1994

Related U.S. Application Data

[60] Continuation of Ser. No. 143,691, Oct. 28, 1993, abandoned, which is a division of Ser. No. 771,597, Oct. 4, 1991, Pat. No. 5,358,612, which is a continuation-in-part of Ser. No. 764,645, Sep. 24, 1991, abandoned.

[51] Int. Cl.$^6$ .................. G01N 27/26; G01N 27/447
[52] U.S. Cl. ........................... 204/299 R; 204/180.1
[58] Field of Search .................... 204/299 R, 180.1

[56] References Cited

FOREIGN PATENT DOCUMENTS 60-57245  4/1985  Japan ......................... 204/299 R

*Primary Examiner*—John Niebling
*Assistant Examiner*—John S. Starsiak, Jr.
*Attorney, Agent, or Firm*—Timothy S. Stevens; Burke M. Hallderson

[57] ABSTRACT

Improved capillary electrophoresis apparatus of the type that generally includes a capillary tube, the capillary tube having a sample inlet end and an outlet end, a first electrode in electrical communication with the inlet end of the capillary tube, a second electrode in electrical communication with the outlet end of the capillary tube and a high voltage power supply in electrical communication with the first and second electrodes. The improvement is to connect a miniature Ion Chromatography membrane suppressor to the outlet end of the capillary tube, to connect a conductivity detector to the membrane suppressor and to place the second electrode in the regenerant compartment of the membrane suppressor. The method embodiment of the invention for anion analysis includes the steps of: (a) separating anions of interest by capillary electrophoresis in a buffer solution; (b) exchanging cations of the buffer for regenerant cations using an ion chromatography membrane suppressor to reduce the electrical conductivity of the buffer to produce a suppressed buffer; and (c) measuring the electrical conductivity of the suppressed buffer to determine the separated anions. Similarly, the method embodiment of the invention for cation analysis includes the steps of: (a) separating cations of interest by capillary electrophoresis in a buffer solution; (b) exchanging anions of the buffer for regenerant anions using a stationary means for exchanging anions thereby reducing the electrical conductivity of the buffer to produce a suppressed buffer; and (c) measuring the electrical conductivity of the suppressed buffer to determine the separated cations.

7 Claims, 3 Drawing Sheets

ELECTROPHORESIS WITH CHEMICALLY SUPPRESSED DETECTION

CROSS-REFERENCE TO RELATED APPLICATIONS

This is a continuation of application Ser. No. 08/143,691, filed Oct. 28, 1993, now abandoned, which is a divisional of application Ser. No. 07/771,597, filed Oct. 4, 1991, now U.S. Pat. No. 5,358,612, which is a continuation-in-part application of U.S. Ser. No. 07/764,645, filed Sep. 24, 1991, now abandoned herein fully incorporated by reference.

BACKGROUND OF THE INVENTION

Electrophoresis is a well developed chemical analysis technique. A review reference on this subject is Chapter 9 of Chromatography—Fundamentals and Applications of Chromatographic and Electrophoretic Methods, Part A: Fundamentals and Techniques, edited by E. Heftmann, Elsevier Scientific Publishing Company, 1983, herein fully incorporated by reference. Capillary electrophoresis (CE) is an important advance in electrophoresis which was pioneered by Jorgenson and Lukacs as reported in Analytical Chemistry 1298 (1981) and in 222 Science 266 (1983), each of which are herein fully incorporated by reference. Since a small diameter capillary is used in CE, a relatively high applied voltage can be used without generating problematic thermal gradients in the capillary. The efficiency of separation in CE is a function of, among other things, the applied voltage. The efficiency of CE is relatively high, e.g., in excess of 400,000 theoretical plates.

The following is a description of a typical CE experiment. A 50–100 micrometer internal diameter silica capillary tube is filled with a suitable conducting buffer. The outlet end of the capillary is immersed in a reservoir containing the buffer and an electrode. A sample containing fluorescent ions of interest is introduced into the inlet end of the capillary and then the inlet end of the capillary is placed into another reservoir containing the buffer and another electrode. A voltage of 30,000 volts is impressed between the electrodes. A fluorescence detector is positioned near the outlet end of the capillary to detect the ions of interest.

The movement of the sample ions of interest is controlled by two factors: (1) electrophoretic migration; and (2) electroosmotic flow. Electrophoretic migration is the migration of the ions of interest towards the oppositely charged electrode under the influence of the electric field. Electroosmotic flow is bulk flow of the buffer in the capillary when the inside surface of the capillary which is in contact with the buffer comprises fixed charge sites which in turn have corresponding mobile counter-ions in the buffer. An unmodified silica capillary surface comprises silanol (Si—OH) groups that are negatively charged (Si—O$^-$) when the pH of the buffer is greater than about 2, and positively charged (Si—OH$_2{}^+$) when the pH of the buffer is less than about 2.

When the surface is negatively charged, then the corresponding mobile counter-ions of the negatively charged surface, e.g., sodium ions (Na+), migrate under the influence of the electric field and in the process drag the bulk solvent with them. Thus, the direction of the electroosmotic flow is from the positive to the negative electrode when the surface is negatively charged.

When the surface is positively charged, then the corresponding mobile counter-ions of the positively charged surface, e.g., biphosphate ions (HPO$_4{}^{-2}$), migrate under the influence of the electric field and in the process drag the bulk solvent with them. Thus the direction of the electroosmotic flow is from the negative to the positive electrode when the surface is positively charged. A positively charged surface can also be obtained, e.g., by adsorbing hydrophobic cations onto the inside surface of the capillary.

When the surface is not charged, then there is no electroosmotic flow. Thus, depending on the charge (positive or negative) of the ions of interest, the nature and extent of capillary surface charging and the polarity of the applied voltage, electroosmosis can augment, counteract or even override the electrophoretic migration. Since sample components to be determined must travel from the inlet end of the capillary to the detector which is located near the outlet end of the capillary, it is essential that they move in the desired direction.

Waters Chromatography Division of Millipore of Milford, Mass. and Dionex Corporation of Sunnyvale, Calif. are the leading domestic manufacturers of CE instruments for the analysis of common ions. The Waters instrument utilizes indirect photometric detection, see for example Jandik et al., LC GC magazine, September 1991 issue, beginning on page 634, herein fully incorporated by reference. The Dionex system uses a photometric detector or a fluorescence detector, see for example the Dionex advertisement in LC GC magazine, September 1991 issue, on page 639, herein fully incorporated by reference. At the present time, the preferred detection method in CE for the determination of common ions is indirect photometric detection.

Even though CE has many advantages, it also has several characteristics that need improvement. For example, the concentration detection limit of CE could be improved.

SUMMARY OF THE INVENTION

The instant invention is the provision of suppressed detection for CE. A primary benefit of the instant invention is improved limits of detection. One apparatus embodiment of the invention is an improved capillary electrophoresis apparatus of the type that generally includes a capillary, the capillary having a sample inlet portion and an outlet portion, a first electrode in electrical communication with the inlet portion of the capillary, a second electrode in electrical communication with the outlet portion of the capillary and a power supply in electrical communication with the first and second electrodes. The improvement comprises means for exchanging ions, the means for exchanging ions being in liquid communication with the capillary, the means for exchanging ions being stationary.

Another apparatus embodiment of the invention is an improved capillary electrophoresis apparatus of the type that generally includes a capillary, the capillary having a sample inlet portion and an outlet portion, a porous conduit means, the channel of the porous conduit means being in liquid communication with the capillary, a first electrode in electrical communication with the inlet portion of the capillary tube, a second electrode in electrical communication with the porous conduit means, a power supply in electrical communication with the first and second electrodes. The improvement comprises means for exchanging ions, the means for exchanging ions being in liquid communication with the channel of the porous conduit means, the means for exchanging ions being stationary.

One method embodiment of the invention is an electrophoresis anion analysis method comprising the steps of: (a) separating anions of interest by electrophoresis in a buffer solution; (b) exchanging cations of the buffer for regenerant cations using a stationary means for exchanging cations thereby reducing the electrical conductivity of the buffer to produce a suppressed buffer; and (c) measuring the electrical conductivity of the suppressed buffer to determine the separated anions.

Another method embodiment of the invention is an electrophoresis cation analysis method comprising the steps of: (a) separating cations of interest by electrophoresis in a buffer solution; (b) exchanging anions of the buffer for regenerant anions using a stationary means for exchanging anions thereby reducing the electrical conductivity of the buffer to produce a suppressed buffer; and (c) measuring the electrical conductivity of the suppressed buffer to determine the separated cations.

DETAILED DESCRIPTION OF THE INVENTION

Figure 1:
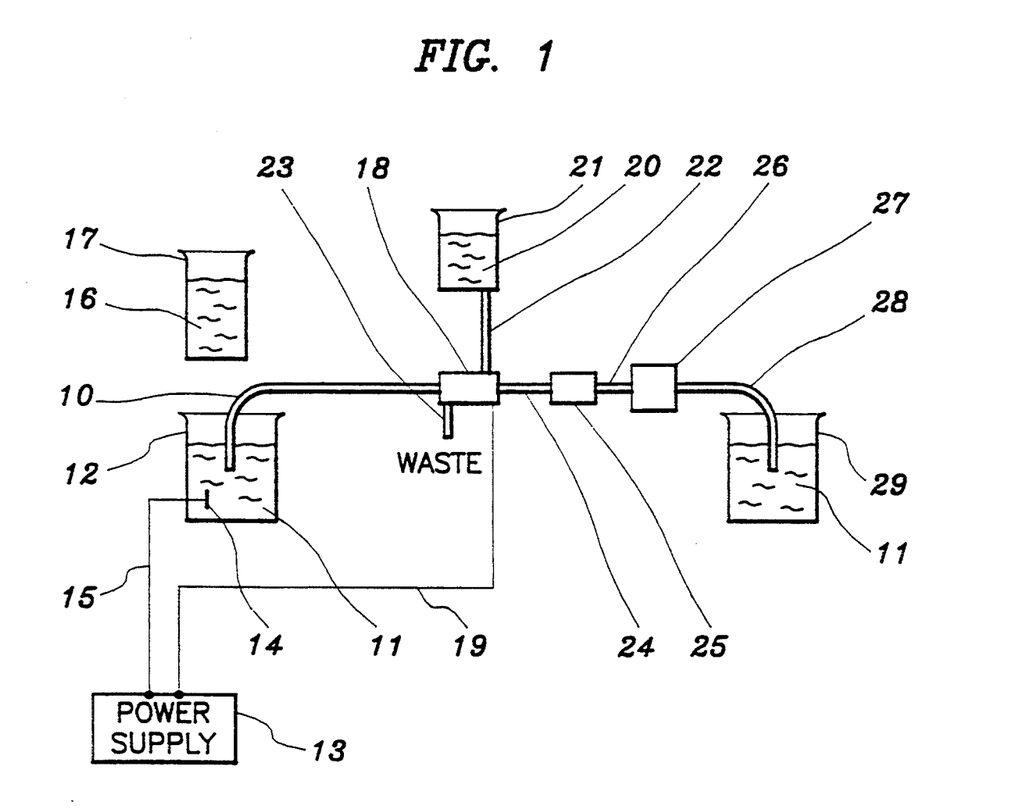
FIG. 1 is a schematic drawing of one apparatus embodiment of the invention.

Referring now to FIG. 1, therein is shown a schematic drawing of an apparatus embodiment of the invention including a fused silica capillary 10. The inlet portion of the capillary 10 is shown immersed in a buffer 11 contained in a first buffer reservoir 12. The buffer 11 is usually water based but can be based on other solvents such as alcohols, acetonitrile, tetrahydrofuran and glycols. A power supply 13 supplies a selected voltage (or current) to a first electrode 14 via a wire 15. A sample to be analyzed 16 is contained in a sample reservoir 17. The sample to be analyzed 16 contains ions of interest. The outlet portion of the capillary 10 is connected to a suppressor 18. The high voltage power supply 13 is connected to the suppressor 18 via a wire 19. A regenerant 20 is contained in a regenerant reservoir 21. A tube 22 connects the reservoir 21 with the suppressor 18. The regenerant 21 flows through the suppressor 18, through a tube 23 to waste. As will be discussed below in detail, the suppressor 18 contains an ion exchange material or means and the regenerant is used to regenerate this ion exchange material or means. A tube 24 connects the suppressor 18 to an electrical conductivity detector 25. A tube 26 connects the conductivity detector 25 to an optional additional detector 27 such as an optical or an electrochemical detector. A tube 28 is shown immersed in buffer 11 contained in a second buffer reservoir 29 and connected to the detector 27. The tube 28 is preferably of a relatively large internal diameter for the reasons to be discussed below. An aliquot of the sample 16 can be introduced into the inlet portion of the capillary 10 by lifting the inlet portion of the capillary 10 from the reservoir 12 temporarily placing it in the sample reservoir 17 and then placing it back into the reservoir 12. This can be done manually but preferably it is done by automated means as is well known in the art. The volume of sample 16 so introduced into the inlet portion of the capillary 10, of course, depends on the length of time the inlet portion of the capillary 10 is immersed into the sample 16 because the level of the sample 16 is higher than the level of the buffer 11 in the second buffer reservoir 29. Alternatively, the sample 16 can be introduced into the inlet portion of the capillary 10 by electrophoretic migration and/or electroosmotic flow, and it should also be possible to use a sample injection valve. The fused silica capillary 10 is preferred in the invention because of its excellent thermal conductivity characteristics as is well known in the art. However, such a capillary is not critical in the invention and the capillary 10 can be made almost any material. Furthermore, although the capillary 10 is preferably circular in cross section, this is not critical either. A single capillary 10 is preferred in the invention but this is also not critical. Thus, the capillary of the invention, in its broadest scope, is a conduit as defined below. The inlet portion of the capillary of the invention is that portion where the sample to be analyzed is introduced. The outlet portion of the capillary of the invention is that portion where electrophoretic zones leave the capillary and enter, e.g., the suppressor. Normally, the inlet portion of the capillary and the outlet portion of the capillary are the opposite ends of the capillary. However, this is not critical in the invention. Thus, for example, it is contemplated in the invention that a sample can be introduced into the middle of a capillary with its cations of interest migrating toward one end of the capillary while its anions of interest migrate toward the other end of the capillary.

Figure 2:
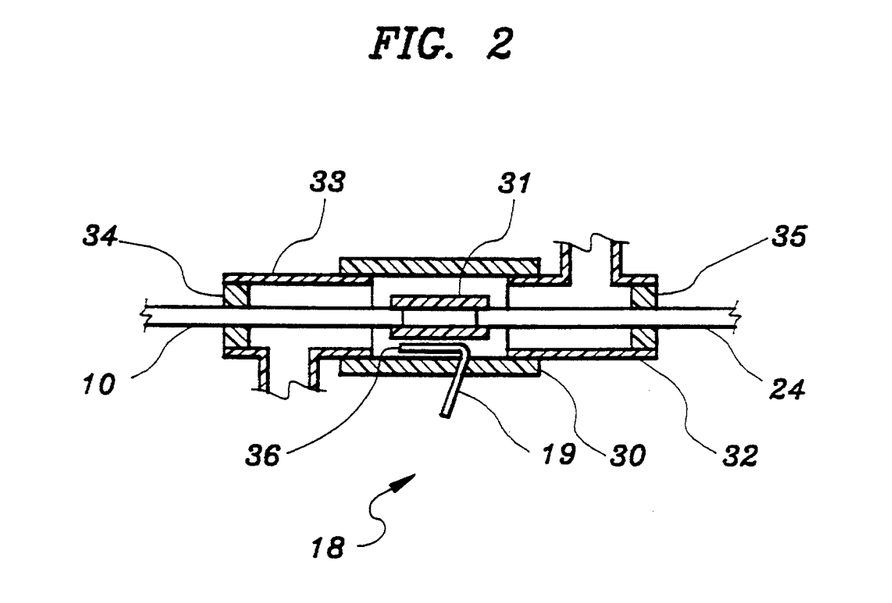
FIG. 2 is a cross-sectional side view of one suppressor embodiment of the invention.

Referring now to FIG. 2, therein is shown a detailed cross-sectional view of the suppressor 18. A tubular jacket 30, made for example of silicone rubber or plasticized polyvinyl chloride, surrounds a length of tubing 31 made of NAFION brand sulfonated fluoropolymer ion exchange material. The outlet portion of the capillary 10 is shown inserted into one end of the of the tubing 31. The tubing 24 is shown inserted into the other end of the tubing 31. A miniature tee 32 is shown inserted into one end of the jacket 30. Another miniature tee 33 is shown inserted into the other end of the jacket 30. The capillary 10 is sealed in the tee 33 by sealant 34 such as room temperature vulcanizing silicone rubber. The capillary tube 24 is sealed in the tee 32 by sealant 35 such as room temperature vulcanizing silicone rubber. A platinum wire 19 is shown inserted through the jacket 30 and the end of the wire 19 within the jacket 30 is the second electrode 36. The electrode 36 can, alternatively, be embedded into the tubing 31 but preferably it is positioned exterior of the tubing 31. In some cases, the electrode 36 is better positioned near the end of the tube 31 where it is connected to the capillary 10. Obviously, the electrode can be positioned in the reservoir 21.

The internal diameter of the tubing 31 preferably is about the same as the internal diameter of the capillary 10. Such small bore ion exchange material is not commercially available. The smallest internal diameter NAFION brand tubing has an internal diameter of about 400 micrometers. However, the internal diameter of such material can be made smaller by a number of techniques such as: (a) by swelling the NAFION tubing in alcohol and then stretching it; (b) heating the NAFION tubing and then stretching it; (c) a combination of (a) and (b); (d) making a small internal diameter tube of NAFION by dipping a small diameter wire, e.g. a 75 micrometer tungsten wire, in a colloidial dispersion of NAFION, thermally curing the NAFION deposited on the wire and then withdrawing the wire from the so formed NAFION tube (U.S. Pat. No. 4,731,263 to Grot, herein fully incorporated by reference, discloses making colloidial dispersions of NAFION as does Martin in Analytical Chemistry 1639 (1982), herein fully incorporated by reference); and preferably by (e) drilling or piercing a small hole through a solid piece of swelled ion exchange material followed by drying to shrink it onto the capillary 10 and the tubing 24.

A conduit is herein defined as any structure having at least one channel therethrough. The tubing 31 is one example of a conduit comprising ion exchange material. However, the invention is not limited to a conduit in the shape of a tube. For example, the conduit can be in the shape of a perforated mass of ion exchange material, e.g., a perforated bead of conventional ion exchange resin such as DOWEX 50W or DOWEX 2 ion exchange resin. A sheet of ion exchange material can be used in a conduit of the invention, e.g., by clamping it between plates having suitable channels and openings. The conduit of the invention preferably comprises an ion exchange material that extends from the channel to the exterior of the conduit. However, the invention will also work when the conduit comprises merely a material that conducts ions or can be made to conduct ions such as cellulose acetate membrane or even porous glass. A porous conduit can be imbibed with a liquid ion exchanger as discussed below.

Figure 3:
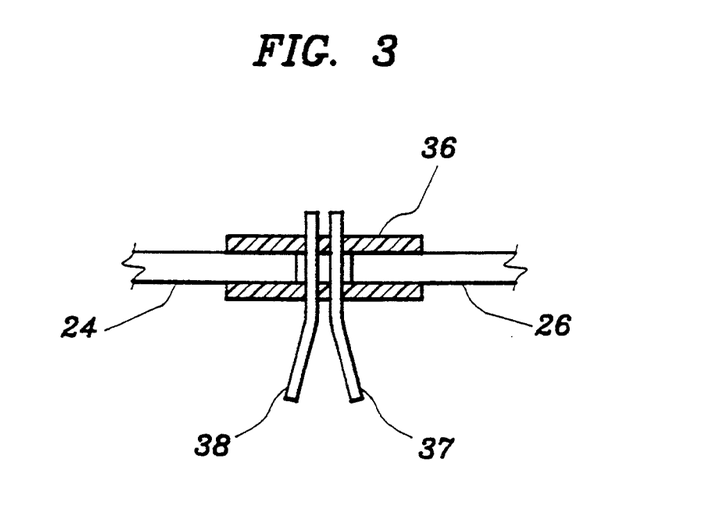
FIG. 3 is a cross-sectional side view of one electrical conductivity cell embodiment of the invention.

Referring now to FIG. 3, therein is shown a detailed cross-sectional view of one embodiment of a cell of the electrical conductivity detector 25. The cell includes a short piece of flexible tubing 36 having a suitably small internal diameter, e.g., 125 micrometers. A fine platinum wire 37 is shown piercing the tubing 36. Another fine platinum wire 38 is also shown piercing the tubing 36. The wires 37 and 38 can be so positioned by first piercing the tubing 36 with a fine hypodermic needle, e.g., a 30 gauge hypodermic needle, inserting the platinum wire into the hypodermic needle and then withdrawing the hypodermic needle while holding the platinum wire in place. The wires 37 and 38 are positioned as close together as possible without touching, e.g., a spacing of 100–300 micrometers. The wires 37 and 38 are the conductivity detector electrodes and are, of course, connected to the electronics portion of a suitable electrical conductivity detector such as an Ion Chromatography electrical conductivity detector.

Figure 4:
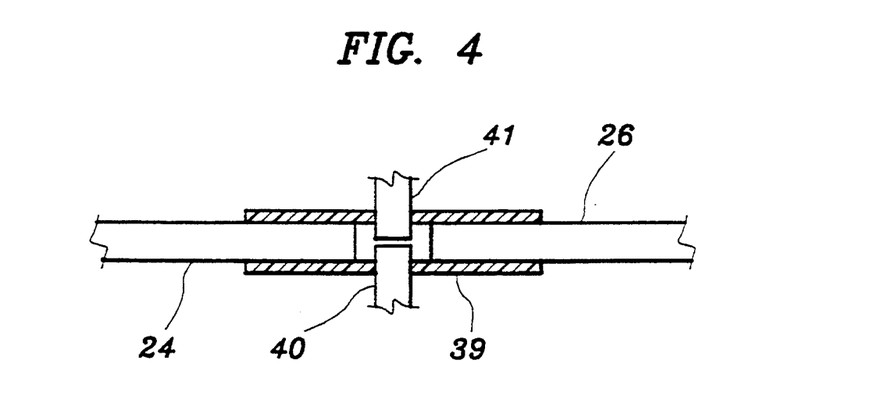
FIG. 4 is a cross-sectional side view of another electrical conductivity cell embodiment of the invention.

Referring now to FIG. 4, therein is shown a detailed cross-sectional view of another embodiment of a cell of the electrical conductivity detector 25. The cell includes a short piece of flexible tubing 39 having a suitably small internal diameter, e.g., 125 micrometers. A stainless steel wire 40 is shown piercing the tubing 39. Another stainless steel wire 41 is shown piercing the tubing 39 on the opposite side of the tubing 39. The ends of the wires 40 and 41 are positioned close together in the tube 39 without touching, e.g., a spacing of 100 micrometers. The wires 40 and 41 are the conductivity detector electrodes and are, of course, connected to the electronics portion of a suitable electrical conductivity detector such as an Ion Chromatography electrical conductivity detector.

Preferably, the resistance to flow of the elements in line after the outlet of the capillary 10 are exceedingly low so as to maintain the flat-fronted flow profile in the capillary 10. Since this ideal is not perfectly attained, it is advantageous to slightly elevate the buffer level in the reservoir 12 relative to the buffer level in the reservoir 29. Alternatively, an additional electrode can be placed in the reservoir 29 and a potential impressed between it and the wire 19 so that there is electroosmotic flow in the elements in line after the outlet of the capillary 10. This alternative is especially applicable when there is no significant inside surface charge on the capillary 10.

Figure 5:
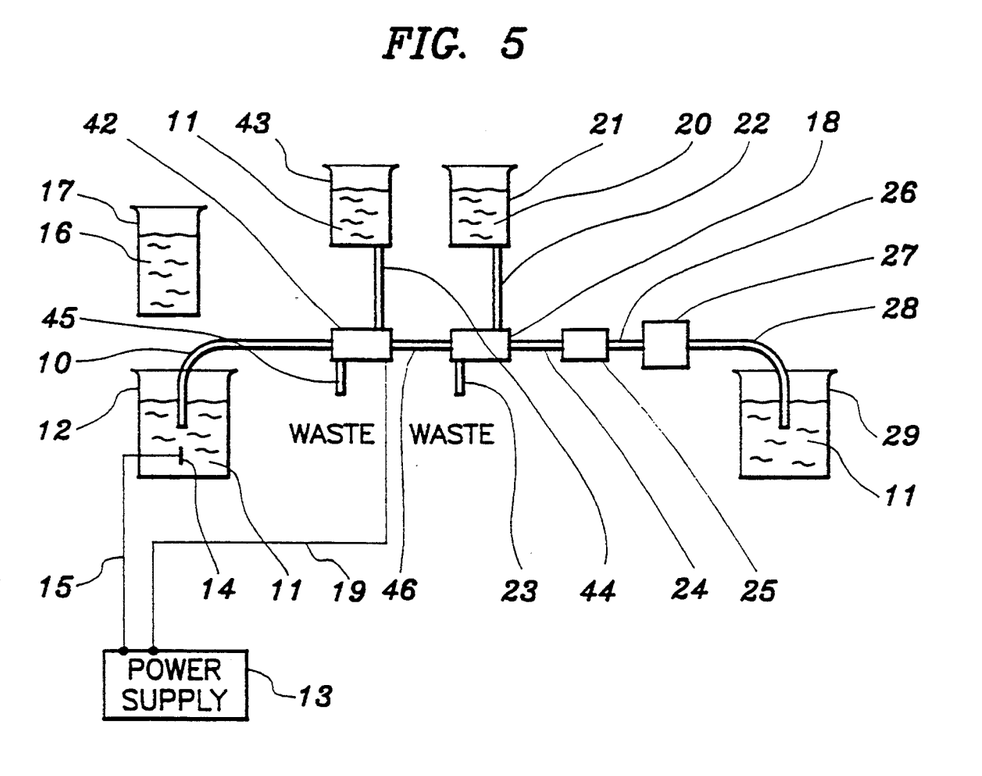
FIG. 5 is a schematic drawing of another apparatus embodiment of the invention.

Referring now to FIG. 5, therein is shown a schematic drawing of another apparatus embodiment of the invention which is similar to the embodiment shown in FIG. 1. The elements shown in FIG. 5 that are the same as the elements shown in FIG. 1 have the same reference numerals. However, it will noticed that in FIG. 5 the wire 19 is no longer directed to the suppressor 18. Instead, the wire 19 is directed to a buffer bridge 42. The buffer 11 is also contained by a third buffer reservoir 43. A tube 44 connects the reservoir 43 with the buffer bridge 42. The buffer 11 in the reservoir 43 flows through the buffer bridge 42, through a tube 45 and then to waste. As will be discussed below in detail, the buffer bridge 42 contains a porous material or other means such as simply a fractured capillary tube (ala Linharcs and Kissinger, Analytical Chemistry 2076 (1991), herein fully incorporated by reference) which provides electrical communication between the buffer within the buffer bridge and the buffer within or exiting the outlet portion of the capillary 10. The buffer bridge is connected to the suppressor 18 by tubing 46.

Figure 6:
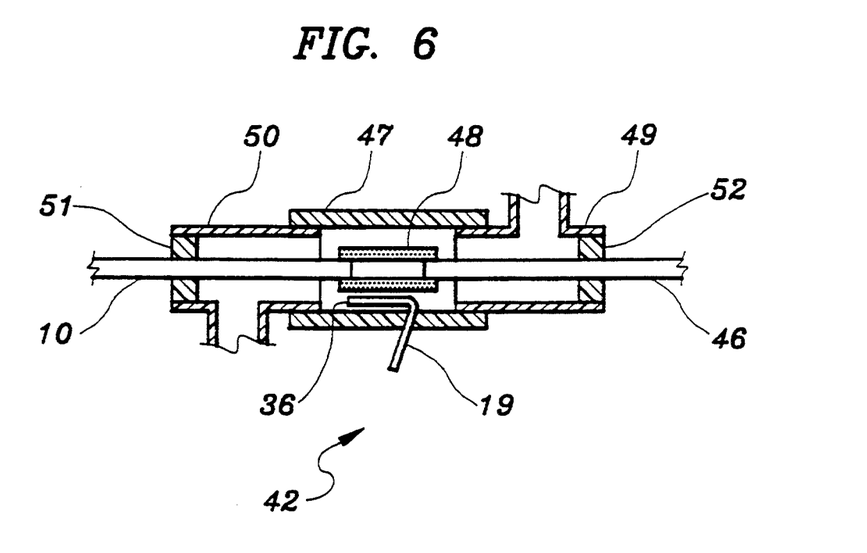
FIG. 6 is a cross-sectional side view of one buffer bridge embodiment of the invention.

Referring now to FIG. 6, therein is shown a detailed cross-sectional view of the buffer bridge 42. The buffer bridge 42 is similar in most respects to the suppressor 18 as will be appreciated by comparing FIG. 6 with FIG. 2. A tubular jacket 47, made for example of silicone rubber or plasticized polyvinyl chloride, surrounds a length of tube made of a porous material such as porous glass. The outlet portion of the capillary 10 is shown inserted into one end of the of the tube 48. The tubing 46 is shown inserted into the other end of the tube 48. A miniature tee 49 is shown inserted into one end of the jacket 47. Another miniature tee 50 is shown inserted into the other end of the jacket 47. The capillary 10 is sealed in the tee 50 by sealant 51 such as room temperature vulcanizing silicone rubber. The capillary tube 46 is sealed in the tee 49 by sealant 52 such as room temperature vulcanizing silicone rubber. A platinum wire 19 is shown inserted through the jacket 47 and the end of the wire 19 within the jacket 47 is the second electrode 36. The electrode 36 can, alternatively, be embedded into the tubing 48 but preferably it is positioned exterior of the tubing 48. Obviously, the electrode 36 can be positioned in the reservoir 43. It will be appreciated that the buffer bridge 42 is similar to the salt bridge of Wallingford and Ewing except that the salt solution (potassium chloride) is being replaced with, e.g., buffer of a suitable concentration or a solution of large ions that can not cross the porous barrier. The tubes 46, 24 and 26 of FIG. 5 as well as the tubes 24 and 26 of FIG. 1 are preferably as short as possible because the flow profile in these tubes is generally parabolic as opposed to the flat-fronted flow profile in the capillary 10.

Means for exchanging ions is defined herein as any means which accepts a cation and in return gives up a cation, any means which accepts an anion and in return gives up an anion and any means which absorbs salts (such as the free base form of DOWEX 4 ion exchange resin which absorbs, e.g., copper nitrate from solution, or such as a crown ether which absorbs salt from solution) including a solid ion exchange material and a liquid ion exchange material. A stationary means for exchanging ions includes the suppressor 18 but also would include a device like the buffer bridge 42 wherein a liquid ion exchanger is positioned within the jacket 47 even though the liquid ion exchanger can be flowed through the device in place of the buffer, i.e., even though the liquid ion exchanger is moving the device is not. Similarly, the porous tube 48 can be imbibed with a liquid ion exchanger and regenerant can be flowed through the device in place of the buffer. A tube containing ion exchange resin is a stationary means for exchanging ions. On the other hand, introducing a suspension of ion exchange particles into the effluent buffer from the capillary tube of a CE system before the buffer flows through a conductivity detector (ala Gjerde and Senson, European Patent Application No. 89110394.7, publication No. 0 345 782 A2, herein fully incorporated by reference) is a mobile means for exchanging ions, i.e., the ion exchange particles move in and with the buffer. Thus, another way of distinguishing the means for exchanging ions of the invention is that the means for exchanging ions of the invention is "non-invasive". A non-invasive means for exchanging ions is a means that is not introduced into the buffer stream, i.e., a means that is not completely surrounded by the buffer stream, and which preferably partitions the buffer stream from a separate source of regeneration cations or anions.

A method embodiment of the invention, with respect to anion analysis, can be understood by reference to FIG. 5. The capillary tube 10 is temporarily immersed in the sample 16 to introduce the sample 16 into the capillary tube 10. The sample contains anions of interest. The buffer 11 contains a salt of a weak acid such as a borate buffer. The ion exchange material of the suppressor 18 is a cation exchanger such a NAFION brand ion exchange material from DuPont. The regenerant 20 is a source of hydrogen ions such as dilute sulfuric acid or a suspension of ion exchange particles in the hydrogen ion form. The power supply 13 is turned on so that the electric field extends from the buffer bridge 42 and along the bore of the capillary 10. If the capillary 10 is negatively charged as discussed above, then the electrode 14 is made positive and the electrode 36 is made negative so that the electroosmotic flow is toward the cation exchange material of the suppressor 18. In addition, if the capillary 10 is negatively charged, then the anions of interest tend to migrate out of the inlet portion of the capillary 10 and into the reservoir 12. This tendency is overcome for many anions of interest by the more rapid electroosmotic flow toward the suppressor 18. If the capillary 10 is positively charged as discussed above, then the electrode 14 is made negative and the electrode 36 is made positive so that the electroosmotic flow is toward the cation exchange material of the suppressor 18. In addition, if the capillary 10 is positively charged, then the anions of interest tend to migrate in the same direction as the electroosmotic flow, i.e., toward the suppressor 18. Thus, there is a distinct benefit in using a positively charged capillary tube 10 in this embodiment. However, this is not critical and there are benefits from using a negatively charged capillary tube 10 in this embodiment. In the suppressor 18, referring now also to FIG. 2, the cations of the buffer are exchanged for hydrogen ions at the inside surface of the ion exchange tube 31 so that the buffer 11 is converted into a weak acid solution to form a suppressed buffer solution. This suppressed buffer solution then flows through the electrical conductivity detector 25. The conductivity of the suppressed buffer, as determined by the detector 25, is relatively low compared to the conductivity of the buffer 11. When the ions of interest flow through the detector 25, they are sensitively detected upon the background of the suppressed buffer. In this respect, the invention is similar to suppressed detection in Ion Chromatography. Hopefully, of course, the ions of interest are resolved into detected separate zones by the prior electrophoresis in the capillary tube 10. The ion exchange material of the suppressor 18 is regenerated by the flow of dilute sulfuric acid regenerant 20 flowing around the exterior of the tube 31. In the above discussion, the buffer comprised a salt of a weak acid. However the invention is not limited to a buffer comprising a salt of a weak acid, e.g., a strong base can be used such as sodium hydroxide which is converted to water by the suppressor. The buffer, when a conductivity detector is used and when its cations are exchanged for the regenerant cations, must be converted to a solution that has reduced electrical conductivity. In this respect, a reference to the suppressed detection Ion Chromatography art will indicate other buffers and regenerant cations that can be used in the invention. The buffer, when another detector is used than a conductivity detector and when its cations are exchanged for the regenerant cations, must be converted to a solution that has a reduced detector response. Most preferably, the anion of the buffer has about the same electrophoretic mobility as the anions of interest.

Another method embodiment of the invention, with respect to anion analysis, can be understood by reference to FIG. 1 and FIG. 2. The capillary tube 10 is temporarily immersed in the sample 16 to introduce the sample 16 into the capillary tube 10. The sample contains anions of interest. The buffer 11 contains a salt of a weak acid such as a borate buffer. The ion exchange material of the suppressor 18 is a cation exchanger such a NAFION brand ion exchange material from DuPont. The regenerant 20 is a source of hydrogen ions such as dilute sulfuric acid or a suspension of ion exchange particles in the hydrogen ion form. The power supply 13 is turned on so that the electric field extends across the ion exchange tube 31 and along the bore of the capillary 10. If the capillary 10 is negatively charged as discussed above, then the electrode 14 is made positive and the electrode 36 is made negative so that the electroosmotic flow is toward the cation exchange material of the suppressor 18. In addition, if the capillary 10 is negatively charged, then the anions of interest tend to migrate out of the inlet portion of the capillary 10 and into the reservoir 12. This tendency is overcome for many anions of interest by the more rapid electroosmotic flow toward the suppressor 18. If the capillary 10 is positively charged as discussed above, then the electrode 14 is made negative and the electrode 36 is made positive so that the electroosmotic flow is toward the cation exchange material of the suppressor 18. In addition, if the capillary 10 is positively charged, then the anions of interest tend to migrate in the same direction as the electroosmotic flow, i.e., toward the suppressor 18. Thus, there is a distinct benefit in using a positively charged capillary tube 10 in this embodiment. However, this is not critical and there are benefits from using a negatively charged capillary tube 10 in this embodiment. In the suppressor 18 the cations of the buffer are exchanged for hydrogen ions at the inside surface of the ion exchange tube 31 so that the buffer 11 is converted into a weak acid solution to form a suppressed buffer solution. If the electrode 36 is negatively charged, then the effectiveness of the suppressor is enhanced. The suppressed buffer solution then flows through the electrical conductivity detector 25. The conductivity of the suppressed buffer, as determined by the detector 25, is relatively low compared to the conductivity of the buffer 11. When the ions if interest flow through the detector 25, they are sensitively detected upon the background of the suppressed buffer. In this respect, the invention is similar to suppressed detection in Ion Chromatography. Hopefully, of course, the ions of interest are resolved into detected separate zones by the prior electrophoresis in the capillary tube 10. The ion exchange material of the suppressor 18 is regenerated by the flow of dilute sulfuric acid regenerant 20 flowing around the exterior of the tube 31. The method embodiment for anion analysis discussed above in reference to FIG. 1 is preferred over the method embodiment for anion analysis discussed above in reference to FIG. 5 as being simpler and probably more effective. In the above discussion, the buffer comprised a salt of a weak acid. However the invention is not limited to a buffer comprising a salt of a weak acid, e.g., a strong base can be used such as sodium hydroxide which is converted to water by the suppressor. The buffer, when a conductivity detector is used and when its cations are exchanged for the regenerant cations, must be converted to a solution that has reduced electrical conductivity. In this respect, a reference to the suppressed detection Ion Chromatography art will indicate other buffers and regenerant cations that can be used in the invention. The buffer, when another detector is used than a conductivity detector and when its cations are exchanged for the regenerant cations, must be converted to a solution that has a reduced detector response. Most preferably, the anion of the buffer has about the same electrophoretic mobility as the anions of interest.

A method embodiment of the invention, with respect to cation analysis, can be understood by reference to FIG. 5. The capillary tube 10 is temporarily immersed in the sample 16 to introduce the sample 16 into the capillary tube 10. The sample contains cations of interest. The buffer 11 contains a salt of a weak base such as a solution aniline hydrochloride or a salt of a zwitterionic compound such as glycinium hydrochloride. The ion exchange material of the suppressor 18 is an anion exchanger such as DOWEX 2 brand ion exchange material from Dow. The regenerant 20 is a source of hydroxide ions such as dilute sodium hydroxide or a suspension of ion exchange particles in the hydroxide ion form. The power supply 13 is turned on so that the electric field extends from the buffer bridge 42 and along the bore of the capillary 10. If the capillary 10 is positively charged as discussed above, then the electrode 14 is negative and the electrode 36 is positive so that the electroosmotic flow is toward the anion exchange material of the suppressor 18. In addition, if the capillary 10 is positively charged, then the cations of interest tend to migrate out of the inlet portion of the capillary 10 and into the reservoir 12. This tendency is overcome for many cations of interest by the more rapid electroosmotic flow toward the suppressor 18. If the capillary 10 is negatively charged as discussed above, then the electrode 14 is positive and the electrode 36 is negative so that the electroosmotic flow is toward the anion exchange material of the suppressor 18. In addition, if the capillary 10 is negatively charged, then the anions of interest tend to migrate in the same direction as the electroosmotic flow, i.e., toward the suppressor 18. Thus, there is a distinct benefit in using a negatively charged capillary tube 10 in this embodiment. However, this is not critical and there are benefits from using a positively charged capillary tube 10 in this embodiment. In the suppressor 18, referring now also to FIG. 2, the anions of the buffer are exchanged for hydroxide ions at the inside surface of the ion exchange tube 31 so that the buffer 11 is converted into a weak base solution to form a suppressed buffer solution. This suppressed buffer solution then flows through the electrical conductivity detector 25. The conductivity of the suppressed buffer, as determined by the detector 25, is relatively low compared to the conductivity of the buffer 11. When the cations if interest flow through the detector 25, they are sensitively detected upon the background of the suppressed buffer. In this respect, the invention is similar to suppressed detection in Ion Chromatography. Hopefully, of course, the cations of interest are resolved into detected separate zones by the prior electrophoresis in the capillary tube 10. The ion exchange material of the suppressor 18 is regenerated by the flow of dilute sodium hydroxide regenerant 20 flowing around the exterior of the tube 31. In the above discussion, the buffer comprised a salt of a weak base. However the invention is not limited to a buffer comprising a salt of a weak base, e.g., a strong acid can be used such as sulfuric acid which is converted to water by the suppressor. The buffer, when a conductivity detector is used and when its anions are exchanged for the regenerant anions, must be converted to a solution that has reduced electrical conductivity. In this respect, a reference to the suppressed detection Ion Chromatography art will indicate other buffers and regenerant cations that can be used in the invention. The buffer, when another detector is used than a conductivity detector and when its anions are exchanged for the regenerant anions, must be converted to a solution that has a reduced detector response. Most preferably, the cation of the buffer has about the same electrophoretic mobility as the cations of interest.

Another method embodiment of the invention, with respect to cation analysis, can be understood by reference to FIG. 1 and FIG. 2. The capillary tube 10 is temporarily immersed in the sample 16 to introduce the sample 16 into the capillary tube 10. The sample contains cations of interest. The buffer 11 contains a salt of a weak base such as a solution aniline hydrochloride or a salt of a zwitterionic compound such as glycinium hydrochloride. The ion exchange material of the suppressor 18 is an anion exchanger such as DOWEX 2 brand ion exchange material from Dow. The regenerant 20 is a source of hydroxide ions such as dilute sodium hydroxide or a suspension of ion exchange particles in the hydroxide ion form. The power supply 13 is turned on so that the electric field extends across the ion exchange tube 31 and along the bore of the capillary 10. If the capillary 10 is positively charged as discussed above, then the electrode 14 is negative and the electrode 36 is positive so that the electroosmotic flow is toward the anion exchange material of the suppressor 18. In addition, if the capillary 10 is positively charged, then the cations of interest tend to migrate out of the inlet portion of the capillary 10 and into the reservoir 12. This tendency is overcome for many anions of interest by the more rapid electroosmotic flow toward the suppressor 18. If the capillary 10 is negatively charged as discussed above, then the electrode 14 is positive and the electrode 36 is negative so that the electroosmotic flow is toward the anion exchange material of the suppressor 18. In addition, if the capillary 10 is negatively charged, then the anions of interest tend to migrate in the same direction as the electroosmotic flow, i.e., toward the suppressor 18. Thus, there is a distinct benefit in using a negatively charged capillary tube 10 in this embodiment. However, this is not critical and there are benefits from using a positively charged capillary tube 10 in this embodiment. In the suppressor 18 the anions of the buffer are exchanged for hydroxide ions at the inside surface of the ion exchange tube 31 so that the buffer 11 is converted into a weak base solution to form a suppressed buffer solution. If the electrode 36 is positively charged, then the effectiveness of the suppressor is enhanced. The suppressed buffer solution then flows through the electrical conductivity detector 25. The conductivity of the suppressed buffer, as determined by the detector 25, is relatively low compared to the conductivity of the buffer 11. When the cations if interest flow through the detector 25, they are sensitively detected upon the background of the suppressed buffer. In this respect, the invention is similar to suppressed detection in Ion Chromatography. Hopefully, of course, the cations of interest are resolved into detected separate zones by the prior electrophoresis in the capillary tube 10. The ion exchange material of the suppressor 18 is regenerated by the flow of dilute sodium hydroxide regenerant 20 flowing around the exterior of the tube 31. The method embodiment for cation analysis discussed above in reference to FIG. 1 is preferred over the method embodiment for cation analysis discussed above in reference to FIG. 5 as being simpler and probably more effective. In the above discussion, the buffer comprised a salt of a weak base. However the invention is not limited to a buffer comprising a salt of a weak base, e.g., a strong acid can be used such as sulfuric acid which is converted to water by the suppressor. The buffer, when a conductivity detector is used and when its anions are exchanged for the regenerant anions, must be converted to a solution that has reduced electrical conductivity. In this respect, a reference to the suppressed detection Ion Chromatography art will indicate other buffers and regenerant cations that can be used in the invention. The buffer, when another detector is used than a conductivity detector and when its anions are exchanged for the regenerant anions, must be converted to a solution that has a reduced detector response. Most preferably, the cation of the buffer has about the same electrophoretic mobility as the cations of interest.

If a neutral capillary is used, then there is no electroosmotic flow in the capillary. If there is no electroosmotic flow in the capillary, then there is no means of transporting the separated ions to the detector. This problem is overcome in the invention, e.g., by introducing a flowing stream of buffer, water or solvent into the outlet portion of the capillary. Referring now to FIG. 5, a tee is placed between the outlet portion of the capillary 10 and the buffer bridge 42. Referring now to FIG. 1, a tee is placed between the outlet portion of the capillary 10 and the suppressor 18. Backflow of this flowing stream of buffer towards the inlet portion of the capillary can be prevented, e.g., by completely filling the reservoir 12 with buffer 11 and then sealing the reservoir 12.

An electrical conductivity detector is preferred in the invention. However, an electrical conductivity detector is not critical in the invention. For example, a photometric detector can be used. Other detectors that can be used include a mass spectrometer, a refractive index detector and a dielectric constant detector. Thus, any detector can be used that detects ions better when the buffer is suppressed.

The capillary of the invention can be negatively charged, positively charged or neutral as discussed above. If the capillary is positively charged and the ions of interest comprise anions or if the capillary is negatively charged and the ions of interest comprise cations, then there can be ion exchange chromatography of the ions of interest as well as electrophoresis of the ions of interest. Usually, most of the separation of the invention is believed to be due to electrophoresis. However, if the capillary of the invention comprises an ion exchange material (such as coating a capillary tube with an ion exchange resin or packing a capillary tube with ion exchange resin beads, a pellicular ion exchanger or a microparticulate ion exchanger), then it is contemplated that ion exchange chromatography can become an important separation mode of the invention.

EXAMPLE 1

The system as generally shown in FIG. 1 is assembled. The capillary 10 is a seventy five micrometer internal diameter fused silica capillary sixty centimeters in length. The tube 31 of FIG. 2 is five millimeters in length and is made by stretching a heated and solvent swollen NAFION tube to an internal diameter of one hundred and twenty five micrometers. The electrode 36 is positioned as shown in FIG. 2 since its polarity helps the effectiveness of the suppressor 18. The regenerant 20 is five millimolar sulfuric acid flowing through the suppressor 18 at a flow rate of one hundred microliters per minute. The buffer 11 is one millimolar borax at a pH of 8.4. Thus, the inside surface of the capillary 10 is negatively charged The sample 16 contains ten milligrams per liter each of monochloroacetate, dichloroacetate and trichloroacetate. The sample is introduced into the capillary 10 by dipping its end into the sample 16, lifting the reservoir 17 ten centimeters above the reservoir 29 for thirty seconds, and then replacing the capillary 10 back into the reservoir 12. Twenty thousand volts positive is applied to the electrode 14. The wire 19 is grounded. A strip chart recorder is connected to the conductivity detector 25 and it records a pherogram showing a peak for trichloroacetate at about three point nine minutes, a peak for dichloroacetate at about four point one minutes and a peak for monochloroacetate at about four point three minutes.

EXAMPLE 2

The experiment of Example 1 is repeated except that the regenerant 20 is mere deionized water. The pherogram shows a peak for monochloroacetate at about three point nine minutes, a peak for dichloroacetate at about four point one minutes and a peak for trichloroacetate at about four point three minutes. This example shows that water can be a source of regenerant hydrogen ions in the invention.

EXAMPLE 3

The system as generally shown in FIG. 1 is assembled. The capillary 10 is a one hundred and fifty micrometer internal diameter fused silica capillary forty centimeters in length. The inside surface of the capillary 10 is made to be positively charged by the following steps: (a) the capillary is filled with a solution of: one percent polyvinyl alcohol that is one hundred percent hydrolyzed; two percent phosphoric acid; one percent poly diallyl dimethyl ammonium chloride; and ninety six percent water; (b) the capillary is placed in an oven at ninety degrees centigrade for two hours; and (c) the capillary is cooled and rinsed with buffer for one hour. The thickness of the resulting modified polyvinyl alcohol coating in the capillary is about one micrometer. The tube 31 of FIG. 2 is five millimeters in length and is made by drilling a block of solvent swollen NAFION and then letting it dry to shrink down onto the capillary 10 and the tube 24. The internal diameter of the resulting channel through the NAFION is about seventy micrometers. The electrode 36 is positioned near the end of the NAFION block that is connected to the capillary 10 so that its influence on the effectiveness of the suppressor is minimized. The regenerant 20 is five millimolar sulfuric acid flowing through the suppressor 18 at a flow rate of one hundred microliters per minute. The buffer 11 is one half millimolar borax at a pH of 8.4. The sample 16 contains ten milligrams per liter each of chloride, nitrate, sulfate and acetate. The sample is introduced into the capillary 10 by dipping its end into the sample 16, lifting the reservoir 17 ten centimeters above the reservoir 29 for thirty seconds, and then replacing the capillary 10 back into the reservoir 12. Twenty thousand volts negative is applied to the electrode 14. The wire 19 is grounded. A strip chart recorder is connected to the conductivity detector 25 and it records a pherogram showing a peak for sulfate at about four point five minutes, a peak for nitrite at about five minutes, a peak for nitrate at about five point three minutes and a peak for acetate at about six minutes. The separation of nitrite and nitrite is greater than expected from the electrophoretic mobilities of these two ions and is explained herein as probably being due to ion exchange chromatography in the capillary 10.

What is claimed is:

1. In an improved capillary electrophoresis apparatus comprising a capillary, the capillary having a sample inlet portion and an outlet portion, a first electrode in electrical communication with the inlet portion of the capillary, a second electrode in electrical communication with the outlet portion of the capillary so that electrical communication between the first and second electrodes comprises a path defined by the channel of the capillary, a power supply in electrical communication with the first and second electrodes and a detector in liquid communication with the outlet portion of the capillary, wherein the improvement comprises positioning a means for exchanging ions between the outlet portion of the capillary and the detector, the means for exchanging ions being a conduit, the conduit comprising an ion exchange material for suppressing a buffer positioned in the channel of the conduit, the channel of the conduit being in liquid communication with the outlet portion of the capillary, the channel of the conduit also being in liquid communication with the detector so that liquid flowing from the outlet portion of the capillary can flow through the conduit to the detector, the second electrode being positioned exterior of the conduit so that the path of the electrical communication between the first and second electrodes further comprises a path across the conduit.

2. The improved capillary electrophoresis apparatus of claim 1, wherein the ion exchange material is an ion exchange membrane, the ion exchange membrane partitioning the outlet portion of the capillary from a regenerate solution holding space defined by a means for containing a regenerate solution, the regenerate solution for regenerating the ion exchange membrane, the ion exchange membrane being capable of exchanging ions of an electrophoresis buffer flowing from the outlet of the capillary for ions in the regenerate solution thereby reducing the detector response of the electrophoresis buffer to produce a suppressed buffer, the second electrode being positioned in the regenerate solution holding space.

3. The improved capillary electrophoresis apparatus of claim 1, further comprising a tube and a third electrode, the tube being in liquid communication with the detector, the third electrode being in electrical communication with the bore of the tube so that there can be electroosmotic flow in the bore of the tube.

4. The improved capillary electrophoresis apparatus of claim 1, wherein the capillary comprises an ion exchange material.

5. In an improved capillary electrophoresis apparatus comprising a capillary, the capillary having a sample inlet portion and an outlet portion, a first electrode in electrical communication with the inlet portion of the capillary, a second electrode in electrical communication with the outlet portion of the capillary so that electrical communication between the first and second electrodes comprises a path defined by the channel of the capillary, a power supply in electrical communication with the first and second electrodes and a detector in liquid communication with the outlet portion of the capillary, wherein the improvement comprises positioning a means for exchanging ions between the outlet portion of the capillary and the detector, the means for exchanging ions being a conduit, the conduit comprising an ion exchange material for suppressing a buffer positioned in the channel of the conduit, the channel of the conduit being in liquid communication with the outlet portion of the capillary, the channel of the conduit also being in liquid communication with the detector so that liquid flowing from the outlet portion of the capillary can flow through the conduit to the detector, the second electrode being embedded in the conduit so that the path of the electrical communication between the first and second electrodes further comprises a path through at least a portion of the conduit.

6. The improved capillary electrophoresis apparatus of claim 5, further comprising a tube and a third electrode, the tube being in liquid communication with the detector, the third electrode being in electrical communication with the bore of the tube so that there can be electroosmotic flow in the bore of the tube.

7. The improved capillary electrophoresis apparatus of claim 5, wherein the capillary comprises an ion exchange material.

* * * * *